United States Patent [19]

Hoffbeck

[11] Patent Number: 5,569,821
[45] Date of Patent: *Oct. 29, 1996

[54] INBRED CORN LINE PHT11

[75] Inventor: Loren J. Hoffbeck, Tipton, Ind.

[73] Assignee: Pioneer Hi-Bred International, Inc., Des Moines, Iowa

[*] Notice: The term of this patent shall not extend beyond the expiration date of Pat. No. 5,434,346.

[21] Appl. No.: 499,517

[22] Filed: Jul. 7, 1995

Related U.S. Application Data

[63] Continuation of Ser. No. 70,488, Jun. 2, 1993, Pat. No. 5,434,346, which is a continuation of Ser. No. 649,789, Feb. 1, 1992, abandoned.

[51] Int. Cl.$^6$ .............................. A01H 4/00; A01H 5/00; C12N 5/04

[52] U.S. Cl. .................. 800/200; 800/250; 800/DIG. 56; 47/58

[58] Field of Search ........................ 800/200, DIG. 56; 435/172.3; 47/58, DIG. 1

[56] References Cited

U.S. PATENT DOCUMENTS 5,434,346  7/1995  Hoffbeck .............................. 800/200

*Primary Examiner*—Gary Benzion

[57] ABSTRACT

According to the invention, there is provided an inbred corn line, designated PHT11. This invention thus relates to the plants and seeds of inbred corn line PHT11 and to methods for producing a corn plant produced by crossing the inbred line PHT11 with itself or with another corn plant. This invention further relates to hybrid corn seeds and plants produced by crossing the inbred line PHT11 with another corn line or plant.

2 Claims, No Drawings

INBRED CORN LINE PHT11

REFERENCE TO RELATED APPLICATIONS

This is a continuation of prior application Ser. No. 08/070,488, filed Jun. 2, 1993, now U.S. Pat. No. 5,434,346, which was a continuation of application Ser. No. 07/649,789, filed Feb. 1, 1992, now abandoned.

FIELD OF THE INVENTION

This invention is in the field of corn breeding, specifically relating to an inbred corn line designated PHT11.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform. number of gene loci will produce a population of hybrid plants that differ genetically and will not be uniform.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHT11. This invention thus relates to the seeds of inbred corn line PHT11, to the plants of inbred corn line PHT11, and to methods for producing a corn plant produced by crossing the inbred line PHT11 with itself or another corn line. This invention further relates to hybrid corn seeds and plants produced by crossing the inbred line PHT11 with another corn line.

DEFINITIONS

In the description and examples that follow, a number of terms are used herein. In order to provide a clear and consistent understanding of the specification and claims, including the scope to be given such terms, the following definitions are provided:

BAR PLT=BARREN PLANTS. This is the percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the inbred or hybrid was grown.

DRP EAR=DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete. % MN is percent of the mean for the experiments in which the inbred or hybrid was grown.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Inbred corn line PHT11 is a yellow, dent corn inbred that is best used as a female in crosses for producing first generation F1 corn hybrids. PHT11 is adapted to most regions of the United States. The inbred can be used to produce hybrids from approximately 106–118 relative maturity based on the Minnesota Relative Maturity Rating System for harvest moisture of grain. PHT11 has good ear retention and excellent grain quality. The inbred has excellent germination and good stalk strength. In hybrid combinations, PHT11 has good yield and rapid drydown in the field. PHT11 is a tall inbred and often fails to silk properly. PHT11 has small kernels and flowers late in relationship to its grain moisture maturity.

The inbred has shown uniformity and stability within the limits of environmental influence for all the traits as described in the Variety Description Information (Table 1) that follows. Most of the data in the Variety Description Information was collected at Johnston, Iowa. The inbred has been self-pollinated and ear-rowed a sufficient number of generations with careful attention paid to uniformity of plant type to ensure homozygousity and phenotypic stability. The line has been increased both by hand and in isolated fields with continued observation for uniformity. No variant traits have been observed or are expected in PHT11.

Inbred corn line PHT11, being substantially homozygous, can be reproduced by planting seeds of the line, growing the resulting corn plants under self-pollinating or sib-mating conditions with adequate isolations, and harvesting the resulting seed, using techniques familiar to the agricultural arts.

TABLE 1

VARIETY DESCRIPTION INFORMATION
INBRED = PHT11

Type: Dent            Region Best Adapted: Most Regions

A. Maturity: Average across maturity zones. Zone: 0

Heat Unit Shed: 1460
Heat Unit Silk: 1480
No. Reps: 61

$$\text{HEAT UNITS} = \frac{[\text{Max. Temp. (}^\circ \leq 86^\circ \text{ F.)} + \text{Min. Temp (}\geq 50^\circ \text{ F.)}]*}{2} - 50$$

B. Plant Characteristics:

Plant height (to tassel tip): 237 cm
Length of top ear internode: 13 cm
Number of ears per stalk: Single
Ear height (to base of top ear): 89 cm
Number of tillers: None
Cytoplasm type: Normal C. Leaf:

Color: Dark Green (B14)
Angle from Stalk: <30 degrees
Marginal Waves: Few (WF9)
Number of Leaves (mature plants): 19
Sheath Pubescence: Light (W22)
Longitudinal Creases: Many (PA11)
Length (Ear node leaf): 79 cm
Width (widest point, ear node leaf): 10 cm D. Tassel:

Number lateral branches: 1
Branch Angle from central spike: 30–40 degrees
Peduncle Length (top leaf to basal branches): 21 cm
Anther Color: Yellow
Glume Color: Green E. Ear (Husked Ear Data Except When Stated Otherwise):

Length: 15 cm
Weight: 101 gm
Mid-point Diameter: 38 mm

TABLE 1-continued

VARIETY DESCRIPTION INFORMATION
INBRED = PHT11

Type: Dent            Region Best Adapted: Most Regions

Silk Color: Green
Husk Extension (Harvest stage): Medium (Barely covering ear)
Husk Leaf: Short (<8 cm)
Taper of Ear: Slight
Position of Shank (dry husks): Upright
Kernal Rows: Straight, Distinct Number = 16
Husk Color (fresh): Light Green
Husk Color (dry): Buff
Shank Length: 10 cm
Shank (No. of internodes): 9
F. Kernel (Dried):

Size (from ear mid-point)
Length: 10 mm
Width: 7 mm
Thick: 4 mm
Shape Grade (% rounds): 20–40 (26% medium round based on Parent Test Data)
Pericarp Color: Colorless
Aleurone Color: Homozygous Yellow
Endosperm Color: Yellow
Endosperm Type: Normal Starch
Gm Wt/100 Seeds (unsized): 23 gm
G. Cob:

Diameter at mid-point: 21 mm
Strength: Strong
Color: Red
H. Diseases:

Corn Lethal Necrosis (MCMV = Maize Chlorotic Mottle Virus and MDMV = Maize Dwarf Mosaic Virus): Intermediate
Maize Dwarf Mosiac Complex (MDMV & MCDV = Maize Dwarf Virus): Susceptible
Anthracnose Stalk Rot (*C. graminicola*): Intermediate
S. Leaf Blight (*B. maydis*): Intermediate
N. Leaf Blight (*E. turcicum*): Intermediate
Common Rust (*P. sorghi*): Intermediate
Southern Rust (*P. polysora*): Susceptible
Gray Leaf Spot (*C. zeae*): Susceptible
Stewart's Wilt (*E. stewartii*): Susceptible
Gross's Wilt (*C. nebraskense*): Resistant
Fusarium Ear Mold (*F. moniliforme*): Resistant
I. Insects:

European Corn Borer-1 Leaf Damage (Pre-flowering): Intermediate
European Corn Borer-2 (Post-flowering): Susceptible
The above descriptions are based on a scale of 1–9, 1 being highly susceptible, 9 being highly resistant.
S (Susceptible): Would generally represent a score of 1–3.
I (Intermediate): Would generally represent a score of 4–5.
R (Resistant): Would generally represent a score of 6–7.
H (Highly Resistant): Would generally represent a score of 8–9. Highly resistant does not imply the inbred is immune.
J. Variety Most Closely Resembling:

| Character | Inbred |
|---|---|
| Maturity | G39 |
| Usage | G39 |

*If maximum is greater than 86 degrees fahrenheit, then 86 is used and if minimum is less than 50, then 50 is used. Heat units accumulated daily and can not be less than 0.

G39 (PVP Certificate No. 8300115) is a Pioneer Hi-Bred International, Inc. proprietary inbred. Data for Items B, C, D, E, F, and G is based primarily on a maximum of four reps from Johnston, Iowa grown in 1989 and 1990, plus description information from the maintaining station.

ELECTROPHORESIS RESULTS

Isozyme Genotypes for PHT11

Isozyme data were generated for inbred corn line PHT11 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHT11 with its parents, G39 and PHG69.

TABLE 2

ELECTROPHORESIS RESULTS FOR PHT11 AND ITS PARENTS G39 AND PHG69

| LOCI | PHT11 | PARENTS | |
|---|---|---|---|
| | | G39 | PHG69 |
| ACP1 | 4 | 4 | 2 |
| ADH1 | 4 | 4 | 4 |
| CAT3 | 9 | 9 | 9 |
| DIA1 | 12 | 8 | 12 |
| GOT1 | 4 | 4 | 4 |
| GOT2 | 2 | 2 | 4 |
| GOT3 | 4 | 4 | 4 |
| IDH1 | 4 | 4 | 4 |
| IDH2 | 6 | 6 | 6 |
| MDH1 | 6 | 6 | 6 |
| MDH2 | 6 | 6 | 3.5 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 8 |
| PGD1 | 2 | 2 | 2 |
| PGD2 | 2.8 | 5 | 2.8 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHT11. Further, both first and second parent corn plants can come from the inbred corn line PHT11. Thus, any such methods using the inbred corn line PHT11 are part of this invention: selfing, backcrosses, hybrid production, crosses to populations, and the like. All plants produced using inbred corn line PHT11 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous *Zea Mays* Genotypes," 165 Planta 322–332 (1985). Thus, another aspect of this invention is to provide cells which upon growth and differentiation produce the inbred line PHT 11.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHT11, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

Inbred and Hybrid Performance of PHT11

In the examples that follow, the traits and characteristics of inbred corn line PHT11 are given as a line and in hybrid combination. The data collected on inbred corn line PHT11 is presented for the key characteristics and traits.

Table 3A compares PHT11 to one of its parents, G39. The results show PHT11 has higher grain yield and test weight, but lower grain harvest moisture than G39. PHT11 has fewer barren plants and better seedling vigor than G39. PHT11 is a taller inbred and flowers (GDU Shed and GDU Silk) earlier than G39. PHT11 has fewer scattergrain, poorer stay green, and is more susceptible to stalk lodging than G39. PHT11 has better resistance to ear mold and first brood European corn borer than G39.

Table 3B contains results comparing PHT11 to its other parent, PHG69. PHT11 has higher grain harvest moisture and lower test weight than PHG69. PHT11 is a taller inbred with higher ear placement and flowers (GDU Shed and GDU Silk) later than PHG69. PHT11 has a significantly better seedling vigor and early stand count than PHG69. PHT11 has significantly better stay green, but is more susceptible to ear mold than PHG69.

Tables 3C through 3D compare PHT11 with other Pioneer proprietary inbreds with similar genetic backgrounds, similar usage and proven performance in the area where PHT11 is adapted.

The results in Table 3C show PHT11 has higher grain yield, grain harvest moisture, and test weight than G50. PHT11 is a significantly taller inbred, has higher ear placement, and flowers (GDU Shed and GDU Silk) later than G50. PHT11 has better seedling vigor and higher stand count than G50. PHT11 has significantly smaller tassels, is less scattergrain, and has better stay green than G50. PHT11 has better resistance to ear mold and Northern leaf blight, but is more susceptible to first brood European corn borer.

Table 3D compares PHT11 to PHP38. PHT11 has significantly lower yield and grain harvest moisture, but higher test weight than PHP38. PHT11 is taller, has higher ear placement, and flowers (GDU Shed) slightly earlier than PHP38. PHT11 has significantly smaller tassels than PHP38. PHT11 has poorer stay green, less resistance to stalk and root lodging, and more resistance to first brood European corn borer than PHP38.

Table 4 compares PHT11 and PHP38 crossed to the same inbred testers. The PHT11 hybrids have lower yield and grain harvest moisture than the PHP38 hybrids. The PHT11 hybrids are taller and have higher ear placement than the PHP38 hybrids. The PHT11 hybrids are more susceptible to stalk and root lodging, but have better grain appearance than the PHP38 hybrids.

Tables 5 through 7 compares a PHT11 hybrid with Pioneer Brand Hybrids 3394, 3357, and 3295, respectively. The hybrids have a parent in common with the PHT11 hybrid other than PHT11. The hybrids are adapted to much of the same area as the PHT11 hybrids. The results in Table 5 show the PHT11 hybrid has lower grain yield and grain harvest moisture than 3394. The PHT11 hybrid is taller with higher ear placement and flowers (GDU Shed) earlier than 3394. The PHT11 hybrid has better grain appearance, but poorer stay green than 3394. The PHT11 hybrid is more susceptible to stalk and root lodging and second brood European corn borer than 3394.

Table 6 compares a PHT11 hybrid to Pioneer Brand Hybrid 3357. The PHT11 hybrid is lower yielding and has lower grain harvest moisture compared to 3357. The PHT11 hybrid is taller, has higher ear placement, and flowers (GDU Shed) later than 3357. The PHT11 hybrid has better grain appearance, but poorer stay green than 3357. The PHT11 hybrid is significantly more susceptible to stalk lodging and second brood European corn borer than 3357.

Table 7, comparing a PHT11 hybrid to Pioneer Brand Hybrid 3295, shows the PHT11 hybrid is higher yielding, but has lower grain harvest moisture than 3295. The PHT11 hybrid is taller with higher ear placement and flowers (GDU Shed) earlier than 3295. The PHT11 hybrid has poorer stay green and is more susceptible to stalk lodging and second brood European corn borer than 3295.

TABLE 3A

PAIRED INBRED COMPARISON DATA
VARIETY #1 = PHT11
VARIETY #2 = G39

| | VAR # | BU ACR ABS | BU ACR % MN | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|
| TOTAL | 1 | 57.4 | 89 | 18.8 | 5.8 | 91.8 | 88.9 | 32.0 | 6.3 | 38.7 | 100.0 | 0.1 | 1465 | 1473 |
| SUM | 2 | 51.3 | 76 | 20.0 | 6.0 | 85.3 | 81.7 | 32.9 | 5.7 | 37.7 | 99.5 | 0.5 | 1552 | 1574 |
| | LOCS | 20 | 20 | 22 | 11 | 13 | 23 | 22 | 36 | 58 | 7 | 18 | 49 | 45 |
| | DIFF | 6.1 | 13 | 1.2 | 0.2 | 6.5 | 7.2 | 1.0 | 0.6 | 1.0 | 0.5 | 0.5 | 87 | 101 |
| | PROB | .187 | .091* | .002# | .640 | .093* | .000# | .119 | .021+ | .136 | .231 | .192 | .000# | .000# |

| | VAR # | POL SC ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TOTAL | 1 | 3.9 | 2.7 | 7.2 | 58.9 | 7.4 | 6.7 | 4.3 | 89.3 | 83.2 | 7.7 | 4.9 | 2.0 | 5.2 | 3.5 |
| SUM | 2 | 5.3 | 5.7 | 6.7 | 57.0 | 6.9 | 5.2 | 6.1 | 96.4 | 80.5 | 6.3 | 4.2 | 4.5 | 4.4 | 3.9 |
| | LOCS | 19 | 21 | 6 | 20 | 14 | 20 | 27 | 15 | 13 | 16 | 6 | 2 | 17 | 11 |
| | DIFF | 1.4 | 3.0 | 0.5 | 1.9 | 0.4 | 1.5 | 1.8 | 7.1 | 2.7 | 1.4 | 0.8 | 2.5 | 0.8 | 0.4 |
| | PROB | .010+ | .000# | .296 | .000# | .142 | .000# | .000# | .001# | .395 | .014+ | .287 | .500 | .014+ | .559 |

* = 10% SIG
+ = 5% SIG
# = 1% SIG

TABLE 3B

PAIRED INBRED COMPARISON DATA
VARIETY #1 = PHT11
VARIETY #2 = PHG69

| | VAR # | BU ACR ABS | BU ACR % MN | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|
| TOTAL SUM | 1 | 57.6 | 117 | 18.6 | 6.0 | 92.9 | 103.3 | 34.5 | 6.3 | 38.6 | 100.0 | 0.3 | 1500 | 1512 |
| | 2 | 55.7 | 117 | 15.9 | 3.5 | 91.7 | 93.0 | 24.3 | 4.3 | 34.5 | 100.0 | 0.9 | 1355 | 1387 |
| | LOCS | 3 | 3 | 3 | 2 | 4 | 2 | 2 | 5 | 7 | 3 | 4 | 3 | 3 |
| | DIFF | 1.9 | 0 | 2.7 | 2.5 | 1.2 | 10.3 | 10.2 | 2.0 | 4.0 | 0.0 | 0.6 | 145 | 125 |
| | PROB | .828 | .983 | .132 | .126 | .802 | .138 | .002# | .011+ | .061* | 1.00 | .296 | .086* | .115 |

| | VAR # | TEX EAR ABS | TST WT ABS | GRN APP ABS | SCT GRN ABS | STA GRN ABS | STK LDG ABS | RT LDG ABS | EAR MLD ABS | ECB 1LF ABS | ECB 2SC ABS |
|---|---|---|---|---|---|---|---|---|---|---|---|
| TOTAL SUM | 1 | 7.5 | 59.0 | 6.8 | 6.5 | 5.8 | 83.2 | 99.6 | 8.0 | 5.0 | 1.5 |
| | 2 | 8.0 | 60.6 | 6.9 | 7.0 | 1.8 | 78.9 | 98.1 | 9.0 | 3.0 | 1.0 |
| | LOCS | 2 | 3 | 3 | 2 | 4 | 3 | 3 | 2 | 1 | 3 |
| | DIFF | 0.5 | 1.5 | 0.0 | 0.5 | 4.0 | 4.3 | 1.5 | 1.0 | 2.0 | 0.5 |
| | PROB | .500 | .266 | .850 | .500 | .002# | .733 | .341 | .000# | | .000# |

* = 10% SIG
+ = 5% SIG
# = 1% SIG

TABLE 3C

PAIRED INBRED COMPARISON DATA
VARIETY #1 = PHT11
VARIETY #2 = G50

| | VAR # | BU ACR ABS | BU ACR % MNS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|
| TO- | 1 | 58.7 | 121 | 19.3 | 5.8 | 90.0 | 89.6 | 29.8 | 5.8 | 30.8 | 100.0 | 0.3 | 1452 | 1462 |
| TAL | 2 | 52.1 | 104 | 17.0 | 5.3 | 90.2 | 69.1 | 28.0 | 3.3 | 23.7 | 99.6 | 1.4 | 1430 | 1456 |
| SUM | LOCS | 5 | 5 | 5 | 12 | 9 | 16 | 15 | 36 | 51 | 4 | 19 | 49 | 47 |
| | DIFF | 6.6 | 17 | 2.2 | 0.6 | 0.1 | 20.5 | 1.7 | 2.5 | 7.2 | 0.4 | 1.1 | 22 | 5 |
| | PROB | .375 | .430 | .045+ | .206 | .975 | .000# | .232 | .000# | .000# | .391 | .135 | .000# | .415 |

| | VAR # | POL SC ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TO- | 1 | 4.5 | 2.8 | 7.3 | 58.3 | 7.4 | 6.9 | 5.3 | 82.0 | 88.5 | 7.9 | 5.4 | 3.0 | 4.9 | 3.7 |
| TAL | 2 | 6.5 | 7.3 | 7.6 | 57.4 | 6.5 | 5.5 | 3.4 | 85.2 | 98.2 | 6.3 | 3.0 | 3.0 | 7.8 | 4.2 |
| SUM | LOCS | 17 | 21 | 8 | 5 | 4 | 23 | 13 | 4 | 4 | 20 | 6 | 1 | 23 | 14 |
| | DIFF | 2.0 | 4.5 | 0.4 | 0.9 | 0.9 | 14 | 2.0 | 3.2 | 9.8 | 1.6 | 2.4 | 0.0 | 2.9 | 0.5 |
| | PROB | .012+ | .000# | .442 | .379 | .113 | .001# | .000# | .619 | .374 | .000# | .022+ | | .000# | .157 |

\* = 10% SIG
+ = 5% SIG
# = 1% SIG

TABLE 3D

PAIRED INBRED COMPARISON DATA
VARIETY #1 = PHT11
VARIETY #2 = PHP38

| | VAR # | BU ACR ABS | BU ACR % MN | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|
| TOTAL | 1 | 57.8 | 87 | 20.1 | 5.5 | 92.6 | 88.9 | 31.2 | 6.1 | 37.7 | 99.8 | 0.3 | 1456 | 1470 |
| SUM | 2 | 73.3 | 109 | 21.8 | 5.4 | 93.2 | 77.5 | 27.5 | 6.0 | 35.3 | 99.9 | 1.8 | 1465 | 1479 |
| | LOCS | 26 | 26 | 28 | 14 | 20 | 31 | 30 | 53 | 83 | 14 | 26 | 74 | 67 |
| | DIFF | 15.4 | 23 | 1.6 | 0.1 | 0.6 | 11.3 | 3.8 | 0.1 | 2.3 | 0.1 | 1.5 | 8 | 9 |
| | PROB | .000# | .001# | .000# | .699 | .755 | .000# | .000# | .520 | .000# | .408 | .072* | .057* | .068* |

| | VAR # | POL SC ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TOTAL | 1 | 4.0 | 2.6 | 7.2 | 58.4 | 7.5 | 6.9 | 4.1 | 89.6 | 83.5 | 7.9 | 4.9 | 2.0 | 5.1 | 3.9 |
| SUM | 2 | 5.1 | 5.5 | 7.4 | 57.9 | 7.0 | 6.4 | 6.2 | 95.0 | 95.1 | 7.7 | 4.6 | 3.5 | 4.0 | 4.2 |
| | LOCS | 27 | 29 | 9 | 26 | 20 | 25 | 33 | 22 | 13 | 21 | 8 | 2 | 26 | 14 |
| | DIFF | 1.1 | 2.8 | 0.2 | 0.5 | 0.6 | 0.5 | 2.2 | 5.4 | 11.5 | 0.3 | 0.4 | 1.5 | 1.2 | 0.4 |
| | PROB | .020+ | .000# | .447 | .066* | .109 | .148 | .000# | .028+ | .025+ | .205 | .442 | .500 | .000# | .447 |

\* = 10% SIG
+ = 5% SIG
# = 1% SIG

TABLE 4

AVERAGE INBRED BY TESTER PERFORMANCE COMPARING PHT11 TO PHP38 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

|  | INBRED | PRM | SEL IND | BU ACR | YLD | MST | PRM SHD | GDU SHD | STK LDG | RT LDG |
|---|---|---|---|---|---|---|---|---|---|---|
| TOTAL | REPLIC. | 381 | 386 | 386 | 366 | 387 | 39 | 105 | 372 | 73 |
| MEAN WTS | PHT11 | 115 | 103 | 155 | 102 | 96 | 118 | 100 | 101 | 98 |
| MEAN WTS | PHP38 | 119 | 109 | 162 | 106 | 103 | 118 | 101 | 103 | 101 |
|  | DIFF. | 4 | 6 | 7 | 5 | 7 | 1 | 0 | 2 | 3 |

|  | INBRED | STA GRN | TST WTA | GRN APP | SDG VGR | EST CNT | STK CNT | PLT HT | EAR HT | DRP EAR | BRT STK |
|---|---|---|---|---|---|---|---|---|---|---|---|
| TOTAL | REPLIC. | 228 | 385 | 298 | 200 | 286 | 406 | 200 | 200 | 258 | 11 |
| MEAN WTS | PHT11 | 105 | 101 | 107 | 108 | 101 | 100 | 102 | 102 | 100 | 101 |
| MEAN WTS | PHP38 | 129 | 101 | 101 | 108 | 101 | 100 | 98 | 98 | 100 | 100 |
|  | DIFF. | 23 | 0 | 5 | 0 | 1 | 0 | 4 | 4 | 0 | 0 |

TABLE 5

PHT11 HYBRID COMPARED TO PIONEER BRAND HYBRID 3394
VARIETY #1 = PHT11 HYBRID
VARIETY #2 = 3394

|  | VAR # | BU ACR ABS | BU ACR % MN | MST ABS | PLT HT ABS | EAR HT ABS | SDG VGR ABS | EST CNT ABS | DRP EAR ABS | GDU SHD ABS |
|---|---|---|---|---|---|---|---|---|---|---|
| TOTAL SUM | 1 | 162.7 | 106 | 19.9 | 102.3 | 49.3 | 6.6 | 60.1 | 99.4 | 1384 |
|  | 2 | 169.5 | 110 | 21.8 | 97.9 | 48.0 | 6.9 | 60.5 | 99.7 | 1402 |
|  | LOCS | 78 | 78 | 78 | 36 | 36 | 41 | 57 | 60 | 18 |
|  | DIFF | 6.8 | 4 | 2.0 | 4.3 | 1.3 | 0.3 | 0.3 | 0.3 | 18 |
|  | PROB | .000# | .000# | .000# | .000# | .033+ | .067* | .535 | .431 | .006# |

|  | VAR # | GRN APP ABS | STA GRN ABS | STK LDG ABS | RT LDG ABS | NLF BLT ABS | ECB 2SC ABS |
|---|---|---|---|---|---|---|---|
| TOTAL SUM | 1 | 7.0 | 5.2 | 91.8 | 96.4 | 8.5 | 4.0 |
|  | 2 | 6.7 | 6.7 | 93.3 | 97.2 | 7.5 | 5.6 |
|  | LOCS | 59 | 39 | 77 | 20 | 1 | 21 |
|  | DIFF | 0.3 | 1.4 | 1.5 | 0.8 | 1.0 | 1.5 |
|  | PROB | .005# | .000# | .227 | .504 |  | .000# |

* = 10% SIG
+ = 5% SIG
# = 1% SIG

TABLE 6

PAIRED INBRED COMPARISON DATA
VARIETY #1 - PHT11 HYBRID
VARIETY #2 - 3357

|  | VAR # | BU ACR ABS | BU ACR % MN | MST ABS | PLT HT ABS | EAR HT ABS | SDG VGR ABS | EST CNT ABS | DRP EAR ABS | GDU SHD ABS |
|---|---|---|---|---|---|---|---|---|---|---|
| TOTAL SUM | 1 | 154.6 | 100 | 20.9 | 98.8 | 44.3 | 6.1 | 59.4 | 99.6 | 1399 |
|  | 2 | 161.8 | 105 | 21.8 | 95.2 | 41.6 | 6.0 | 60.3 | 99.6 | 1388 |
|  | LOCS | 71 | 71 | 71 | 37 | 37 | 34 | 49 | 48 | 18 |
|  | DIFF | 7.2 | 4 | 0.8 | 3.6 | 2.7 | 0.1 | 1.0 | 0.0 | 11 |
|  | PROB | .001# | .001# | .000# | .000# | .000# | .620 | .182 | .919 | .105 |

|  | VAR # | GRN APP ABS | STA GRN ABS | STK LDG ABS | RT LDG ABS | ECB 2SC ABS |
|---|---|---|---|---|---|---|

TABLE 6-continued

| TOTAL SUM | 1 | 7.9 | 5.5 | 92.1 | 99.4 | 2.8 |
|---|---|---|---|---|---|---|
| | 2 | 7.6 | 6.3 | 94.6 | 98.9 | 3.8 |
| | LOCS | 53 | 40 | 67 | 13 | 20 |
| | DIFF | 0.3 | 0.8 | 2.4 | 0.5 | 1.0 |
| | PROB | .009# | .000# | .014+ | .201 | .030+ |

* = 10% SIG
+ = 5% SIG
# = 1% SIG

TABLE 7

PAIRED INBRED COMPARISON DATA
VARIETY #1 = PHT11 HYBRID
VARIETY #2 = 3295

| | VAR # | BU ACR ABS | BU ACR % MN | MST ABS | BAR PLT ABS | PLT HT ABS | EAR HT ABS | SDG VGR ABS | EST CNT ABS | DRP EAR ABS | GDU SHD ABS |
|---|---|---|---|---|---|---|---|---|---|---|---|
| TOTAL SUM | 1 | 154.8 | 107 | 21.0 | 96.3 | 117.8 | 53.6 | 5.8 | 56.7 | 99.2 | 1406 |
| | 2 | 149.4 | 104 | 22.3 | 91.7 | 115.3 | 52.4 | 6.1 | 56.4 | 98.7 | 1433 |
| | LOCS | 55 | 55 | 55 | 3 | 22 | 22 | 26 | 39 | 25 | 19 |
| | DIFF | 5.5 | 4 | 1.3 | 4.6 | 2.5 | 1.2 | 0.2 | 0.3 | 0.6 | 27 |
| | PROB | .013+ | .058* | .000# | .542 | .004# | .026+ | .269 | .695 | .321 | .007# |

| | VAR # | GRN APP ABS | STA GRN ABS | STK LDG ABS | RT LDG ABS | ECB 2SC ABS |
|---|---|---|---|---|---|---|
| TOTAL SUM | 1 | 6.6 | 5.1 | 88.8 | 83.0 | 4.6 |
| | 2 | 6.3 | 6.1 | 95.0 | 88.3 | 5.6 |
| | LOCS | 43 | 24 | 50 | 23 | 14 |
| | DIFF | 0.2 | 1.0 | 6.2 | 5.3 | 1.1 |
| | PROB | .258 | .000# | .000# | .117 | .027+ |

* = 10% SIG
+ = 5% SIG
# = 1% SIG

Deposits

Applicant has made a deposit of at least 2500 seeds of Inbred Corn Line PHT11 with the American Type Culture Collection (ATCC), Rockville, Md. 20852 USA, ATCC Deposit No. 75962. The seeds deposited with the ATCC on Dec. 7, 1994, were taken from the deposit maintained by Pioneer Hi-Bred International, Inc., 700 Capital Square, 400 Locust Street, Des Moines, Iowa 50309-2340 since prior to the filing date of this application. This deposit of the Inbred Corn Line PHT11 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C. F. R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.). Applicant has applied for U.S. Plant Variety Protection of PHT11 under Application No. 9100101.

What is claimed is:

1. Plant parts of a plant produced by a seed designated PHT11 and having ATCC accession number 75962.

2. Plant parts of a $F_1$ hybrid corn plant grown from a $F_1$ hybrid corn seed produced by crossing inbred corn plant PHT11, having ATCC accession number 75962, with another corn plant that is not PHT11.

* * * * *